US009861803B2

(12) United States Patent
Whitley

(10) Patent No.: US 9,861,803 B2
(45) Date of Patent: Jan. 9, 2018

(54) CATHETER ADAPTER ASSEMBLY AND SYSTEM

(71) Applicant: TELEFLEX MEDICAL INCORPORATED, Research Triangle Park, NC (US)

(72) Inventor: Kenneth W. Whitley, Youngsville, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 438 days.

(21) Appl. No.: 14/554,674

(22) Filed: Nov. 26, 2014

(65) Prior Publication Data

US 2015/0148747 A1    May 28, 2015

Related U.S. Application Data

(60) Provisional application No. 61/909,665, filed on Nov. 27, 2013.

(51) Int. Cl.
*A61M 39/10* (2006.01)
*A61M 25/02* (2006.01)

(52) U.S. Cl.
CPC ........ *A61M 39/1011* (2013.01); *A61M 25/02* (2013.01); *A61M 2025/024* (2013.01); *A61M 2025/0266* (2013.01); *A61M 2039/1022* (2013.01); *A61M 2039/1077* (2013.01)

(58) Field of Classification Search
CPC .............. A61M 39/1011; A61M 25/02; A61M 2025/024; A61M 2025/0266; A61M 2039/1077; A61M 2039/1022
See application file for complete search history.

(56) References Cited

U.S. PATENT DOCUMENTS

| 4,711,636 A | * | 12/1987 | Bierman | ............... | A61M 25/02 128/DIG. 26 |
| 4,889,527 A | | 12/1989 | Herrli | | |
| 5,314,411 A | * | 5/1994 | Bierman | ............... | A61M 25/02 604/174 |

(Continued)

OTHER PUBLICATIONS

International Search Report and Written Opinion revived in corresponding PCT/US14/67626 application dated Feb. 25, 2015 (12 pages).

*Primary Examiner* — Imani Hayman
*Assistant Examiner* — Hamza Darb
(74) *Attorney, Agent, or Firm* — Baker & Hostetler LLP

(57) ABSTRACT

A catheter adapter assembly includes an adapter body and a slider body. The adapter body includes a distal end portion configured to receive a catheter, a coupling disposed on the distal end portion, and a fitting on the proximal end portion. The slider body is disposed about the adapter body and axially slides along the adapter body. The slider body includes a release, a latch disposed at a distal end of the release, and a flexing portion disposed at a proximal end of the release. The slider body also includes compression element that compresses the tubular catheter receiver in response engagement of the latch and the coupling. A catheter adapter system comprising the catheter adapter assembly and a nest that holds the catheter adapter assembly is also disclosed.

16 Claims, 8 Drawing Sheets

(56) References Cited

U.S. PATENT DOCUMENTS

| | | | | |
|---|---|---|---|---|
| 5,992,899 A | * | 11/1999 | Strowe | A61M 39/12 285/338 |
| 2010/0191193 A1 | * | 7/2010 | Pajunk | A61M 25/0014 604/250 |
| 2011/0270230 A1 | * | 11/2011 | Sage | A61M 39/12 604/533 |

* cited by examiner

CATHETER ADAPTER ASSEMBLY AND SYSTEM

CROSS REFERENCE TO RELATED APPLICATION

This application claims the benefit of U.S. Provisional Application No. 61/909,665, filed on Nov. 27, 2013, the disclosure of which is hereby incorporated by reference in its entirety.

FIELD OF THE INVENTION

This disclosure generally relates to medical catheters. More particularly, a catheter adapter assembly and system for securing medical catheters is described.

BACKGROUND OF THE INVENTION

A number of medical procedures involve the catheterization of patients for various applications. One such application is the administration of anesthesia either in advance of, during, or following a particular medical procedure. Often, anesthesia is administered continuously, or at regular intervals, to maintain the effects of the anesthesia during an extended medical procedure. Other applications include various vascular procedures, various intra-uterine procedures, transfusions, etc. A particular type or technique of vascular procedure is the so-called "through the needle" introduction technique.

This technique generally involves the use of a needle capable of being suitably positioned in a patient's body to enable a flexible catheter to be threaded through the needle so that a distal end of the catheter is appropriately lodged in position within the patient's body, and so that a proximal end of the catheter extends from the patient's body. After appropriate positioning of the catheter, the needle is removed from the patient's allowing the distal portions of the catheter to remain in position, and permitting proximal portions of the catheter to freely extend from the patient's body so that subsequent movement of the patient will not cause the distal portions of the catheter to become dislodged from the patient. Anesthetic or other desired medicaments are then introduced to the patient by means of the catheter in conventional fashion.

While this technique is well known, a number of unresolved issues remain with conventional catheter adapters. In particular, conventional catheter adapters either lack a lock or the lock is not secure and is difficult to operate. Accordingly, there is a need to improve catheter adapters.

SUMMARY OF THE INVENTION

The foregoing needs are met, to a great extent, by a catheter adapter assembly and system as described below. In some aspects, a catheter adapter assembly includes an adapter body and a slider body. The adapter body has proximal and distal ends and the distal end portion is configured to receive a catheter, a coupling is disposed on the distal end portion, and a fitting is on the proximal end portion and configured to connect to a fluid line. The slider body is disposed about the adapter body and is configured to axially slide relative to the adapter body. The slider body includes a release and a compression element. The release includes a latch disposed at a distal end of the release and a flexing portion disposed at a proximal end of the release. The latch is configured to engage the coupling of the adapter body to prevent axial movement of the slider body relative to the adapter body. The compression element is configured to compress against the catheter in response to engagement of the latch of the slider body and the coupling of the adapter body.

Implementations may include one or more of the following features. The catheter adapter assembly can further include a tubular catheter receiver within the adapter body, where the tubular catheter receiver is compressed by the compression element in response to the engagement of the latch of the slider body and the coupling of the adapter body. The center axis of the tubular catheter receiver can be aligned with the center axis of the distal end portion of the adapter body. The distal end portion of the adapter body, the tubular catheter receiver, and the fitting of the adapter body can be in fluid communication with one another. The tubular catheter receiver can be an elongated hollow tube made of a deformable material. The inner diameter of the tubular catheter receiver can be slightly greater than the outer diameter of the catheter.

The catheter adapter assembly can further include at least one grip on the outer surface of the slider body. The at least one grip can extend radially from the outer surface of the slider body. The compression element can include at least one gripper extending radially inward, where the at least one gripper can have an axial length that is less than the axial length of the compression element. The release can include at least one hump between the latch and the flexing portion.

The adapter body can further include a stop distal of the fitting, where the stop is configured to prevent proximal movement of a proximal end of the catheter. The stop can include an orifice configured to allow fluid flow through the stop. The coupling can define a recess formed in the adapter body configured to receive the release of the slider body.

The catheter adapter assembly can further include a conductive tab extending from the adapter body, where the conductive tab is configured to conduct an electrical stimulus to the catheter or to fluid flowing within the adapter body in contact with the conductive tab. The conductive tab can be a stop configured to prevent proximal movement of a proximal end of the catheter. The compression element of the slider body can include a first sloped face and a flat face directly distal of the sloped face. The slider body can include a second sloped face configured to mate with the first sloped face of the compression element.

A catheter adapter system is also described. The catheter adapter system includes a catheter adapter assembly and a nest. The catheter adapter assembly includes an adapter body and a slider body. The adapter body has proximal and distal ends and the distal end portion is configured to receive a catheter, a coupling is disposed on the distal end portion, and a fitting is on the proximal end portion and configured to connect to a fluid line. The slider body is disposed about the adapter body and is configured to axially slide relative to the adapter body. The slider body includes a release and a compression element. The release includes a latch disposed at a distal end of the release and a flexing portion disposed at a proximal end of the release. The latch is configured to engage the coupling of the adapter body to prevent axial movement of the slider body relative to the adapter body. The compression element is configured to compress against the catheter in response to engagement of the latch of the slider body and the coupling of the adapter body. The nest includes a base and a receiver configured to receive the catheter adapter assembly on a top side of the base.

Implementations may include one or more of the following features. A bottom side of the base can include an adhesive for securing the base to a patient or an object. The catheter adapter system can further include a catheter and a fluid supply line.

There has thus been outlined, rather broadly, certain aspects of the catheter adapter assembly and system in order that the detailed description thereof herein may be better understood, and in order that the present contribution to the art may be better appreciated. There are, of course, additional aspects of the catheter adapter assembly and system that will be described below and which will form the subject matter of the claims appended hereto.

In this respect, before explaining at least one implementation of the catheter adapter assembly and system in detail, it is to be understood that the catheter adapter assembly and system is not limited in its application to the details of construction and to the arrangements of the components set forth in the following description or illustrated in the drawings. The catheter adapter assembly and system is capable of implementations in addition to those described and of being practiced and carried out in various ways. Also, it is to be understood that the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the catheter adapter assembly and system. It is important, therefore, that the claims be regarded as including such equivalent constructions insofar as they do not depart from the spirit and scope of the catheter adapter assembly and system.

DETAILED DESCRIPTION

A catheter adapter assembly and system described below is configured to passively lock the catheter to prevent accidental openings through the use of a latch. In some arrangements, the catheter adapter assembly is configured to be biased in the open position when opened and in the closed position when closed. The catheter adapter assembly may include a latch that passively locks in response to a catheter being sealed within the catheter adapter assembly. In this or other implementations, the latch may be unlocked by releasing the latch to, in turn, release the catheter from the catheter adapter assembly.

The catheter adapter system may include a nest to secure the catheter adapter assembly. In some implementations, holders may to secure the catheter itself and/or other lines to and from the catheter adapter assembly. In addition, a base may be used to secure the catheter adapter assembly to a patient or an object using, for example, an adhesive surface.

Figure 1:
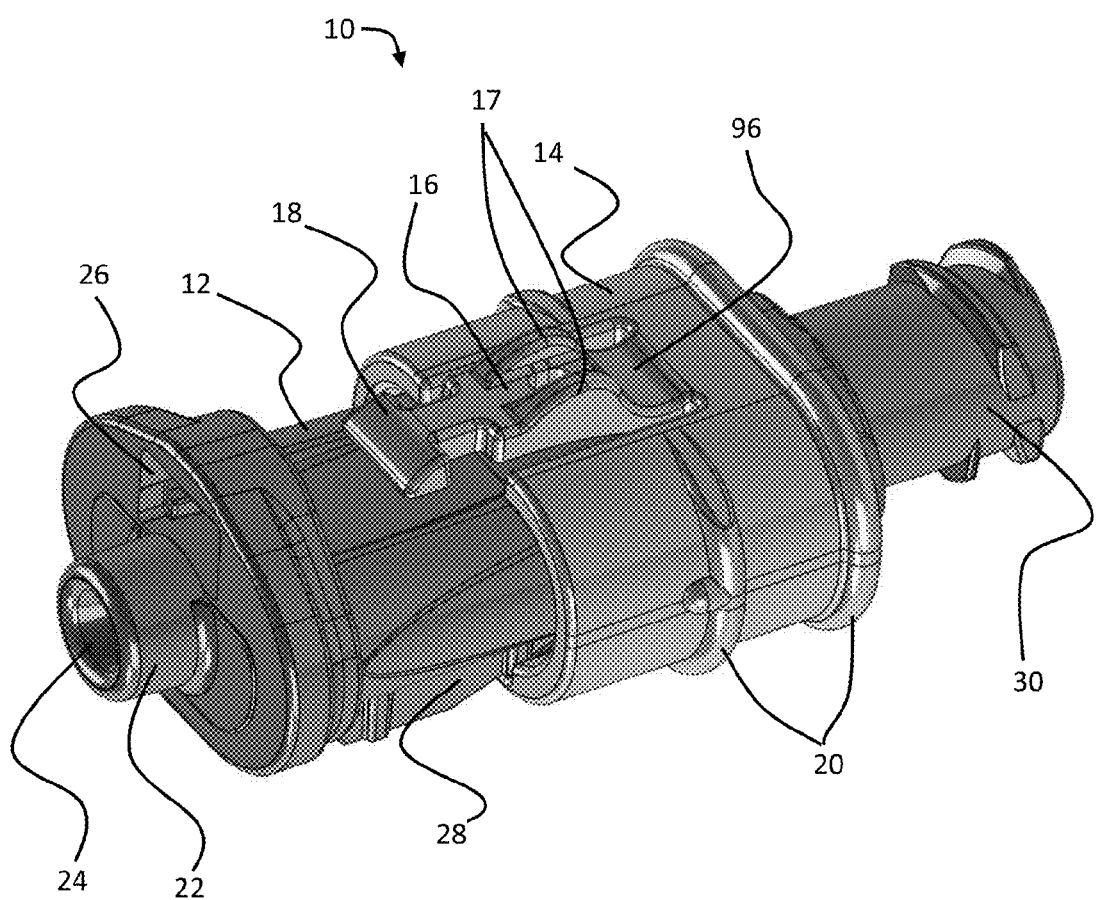
FIG. 1 is a front perspective view of a catheter adapter assembly according to one implementation.

Referring to FIG. 1, a front perspective view of a catheter adapter assembly 10 is illustrated. As shown in FIG. 1, the catheter adapter assembly 10 includes an adapter body 12 and a slider body 14. The slider body 14 includes a release 16, a latch 18, and at least one grip 20. The release 16 comprises at least one hump 17 radially extending from the release 16. Although two grips 20 are shown in FIG. 1 that each extend radially from the outer surface of the slider body 14, in some aspects, the grip 20 may be features formed within the outer surface of the slider body 14, such as a textured surface. Adapter body 12 includes a distal end portion 22 having a catheter insertion guide 24, a coupling 26, a compression element 28, and a proximal fitting 30. The proximal fitting 30 may include any suitable fitting such as a Luer lock, Luer taper (male or female), or the like to receive a fluid source, such as a syringe. The slider body 14 is configured to slide axially along the adapter body 12 in response to force applied by a practitioner by flexing at a flexing portion 96. The latch 18 is configured to lockingly engage the coupling 26. In particular, the catheter adapter assembly 10 is locked when the latch 18 is received within the coupling 26. As shown herein, the release 16 is configured to disengage the latch 18 from the coupling 26. The release 16 can be manipulated inwards, towards the center axis of the catheter adapter assembly 10, in response to force applied by the practitioner. The grips 20 are configured to provide a gripping surface for sliding the slider body 14 axially along the adapter body 12. As shown herein, sliding the slider body 14 distally towards the distal end portion 22 urges the compression element 28 inward towards the center axis of the catheter adapter.

The various components of the catheter adapter assembly 10 may be made from any suitable material. Examples of suitable materials include plastics or other polymers, resins, metals, or the like. In a particular example, the adapter body 12 and slider body 14 may be made from a plastic such as nylon or other thermoplastic. These components may be formed in any suitable manner. Examples of suitable forming methods may include, for example, injection molding, milling, or the like.

Figure 2:
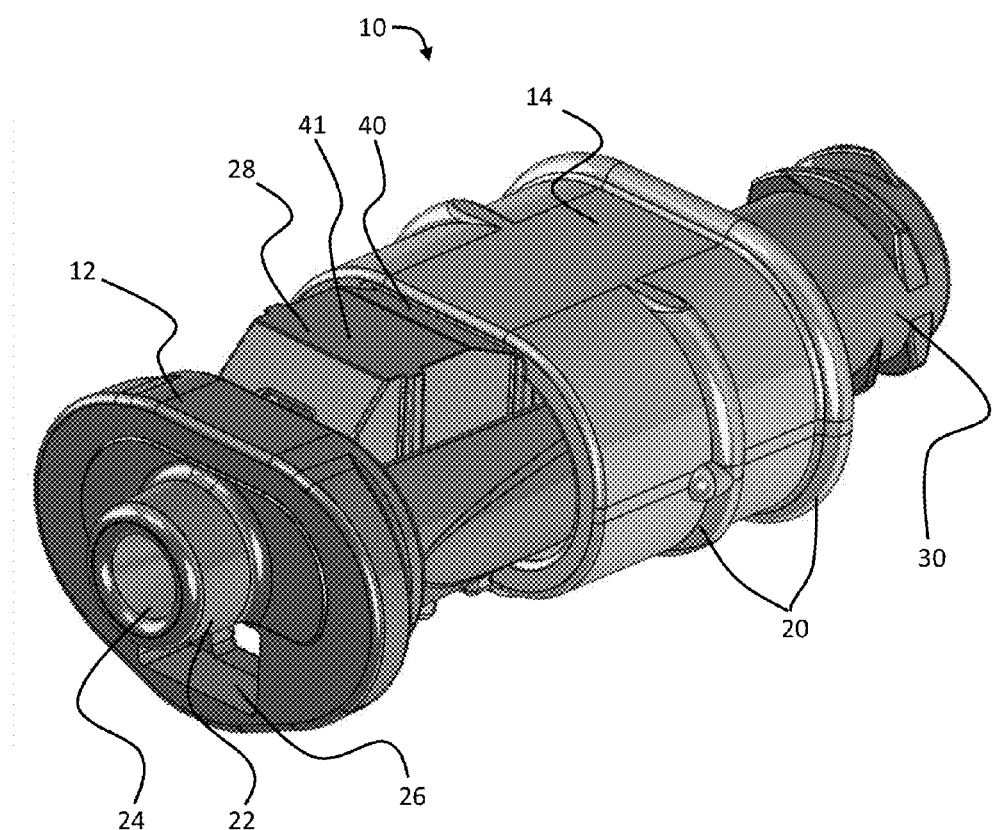
FIG. 2 is a front/inverted perspective view of the catheter adapter assembly according to the implementation of FIG. 1.

FIG. 2 illustrates a front/inverted perspective view of the catheter adapter assembly 10 according to the implementation of FIG. 1. As shown in FIG. 2, the compression element 28 includes a sloped face 40 configured to engage the slider body 14 and a flat face 41 directly distal of the sloped face 40. In response to the slider body 14 distally sliding towards the distal end portion 22, the compression element 28 is configured to move inwards towards the center axis of the catheter adapter assembly 10.

Figure 3:
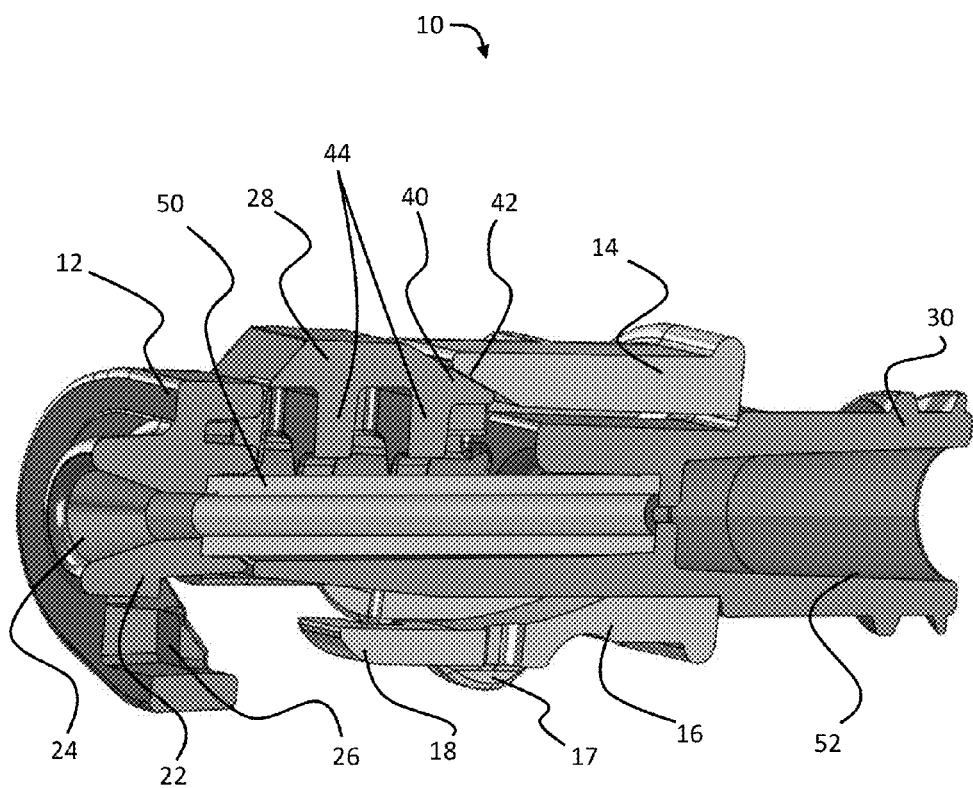
FIG. 3 is a front/inverted cutaway perspective view of the catheter adapter assembly in an open position according to the implementation of FIG. 1.

FIG. 3 illustrates a front/inverted cutaway perspective view of the catheter adapter assembly 10 in an open position according to an implementation of FIG. 1. As shown in FIG. 3, the slider body 14 includes the slider body sloped face 42 configured to mate with a sloped face 40 of the compression element 28. Also shown in FIG. 3, the compression element 28 includes at least one gripper 44 configured to urge against a tubular catheter receiver 50 in response to the compression element 28 being driven towards the tubular catheter receiver 50. The tubular catheter receiver 50 is aligned with the catheter insertion guide 24. In other words, the tubular catheter receiver 50 can share the same center axis as the catheter insertion guide 24. The catheter insertion guide 24 may include a conical forcing cone configured to guide a catheter towards the tubular catheter receiver 50. In addition, the proximal fitting 30 can be a female fitting 52, as shown in FIG. 3, or a male fitting. The tubular catheter receiver 50 may be made of any suitable material, such as silicone, rubber, fluoropolymer, elastomeric or other deformable materials.

In some implementations, the inner diameter of the tubular catheter receiver 50 can be approximately equal to slightly greater than the outer diameter of the catheter. In addition, the inner diameter of the tubular catheter receiver 50 can be equal to the inner diameter of the proximal end of the catheter insertion guide 24.

Figure 4:
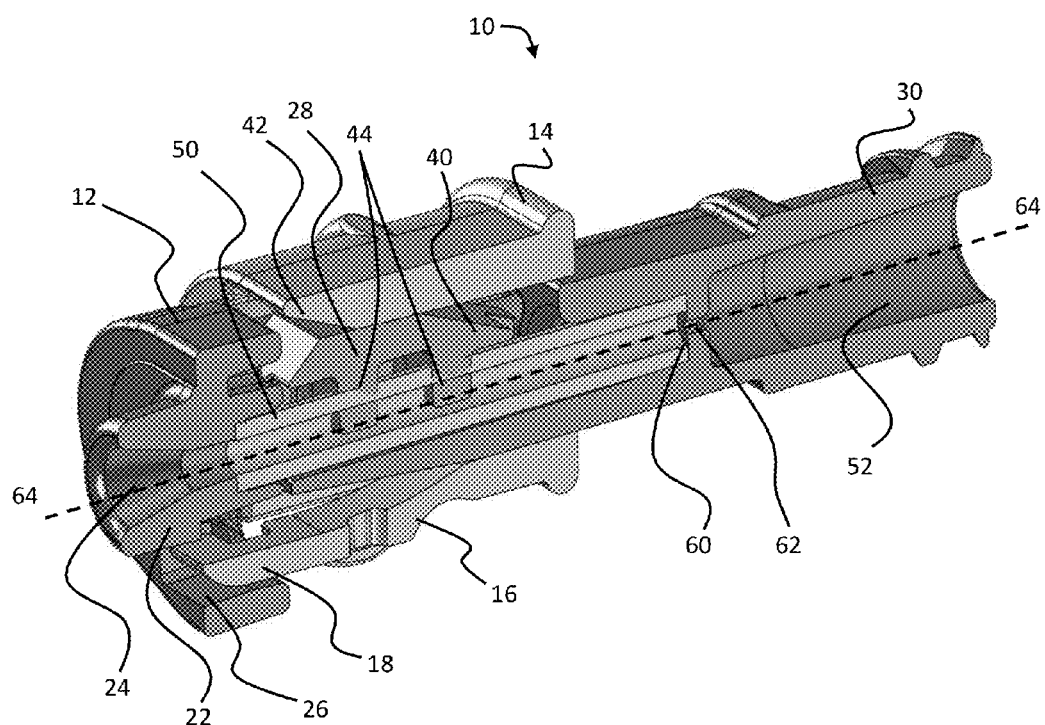
FIG. 4 is a front/inverted partial cutaway perspective view of the catheter adapter assembly in a closed position according to the implementation of FIG. 1.

FIG. 4 illustrates a front/inverted cutaway perspective view of the catheter adapter assembly 10 in a closed position according to the implementation of FIG. 1. As shown in FIG. 4, in response to the slider body 14 distally sliding towards the distal end portion 22, the compression element 28 is driven inwards and the grippers 44 deform the tubular catheter receiver 50, thereby reducing the inner diameter of the tubular catheter receiver 50. As explained above, because the inner diameter of the tubular catheter receiver 50 is approximately equal to slightly greater than the outer diameter of the catheter, a catheter inserted into the tubular catheter receiver 50 will also be compressed in response to the sliding of the slider body 14.

Also shown in FIG. 4, the latch 18 is configured to automatically engage the coupling 26 in response to the slider body 14 distally sliding towards the distal end portion 22. Once closed, the slider body 14 is biased to remain in the closed position due to the engagement of the latch 18 and the coupling 26. In order to move the slider body 14 to its open position, the release 16 may be forced downward to urge the latch 18 to disengage with the coupling 26. While in this disengaged position, the slider body 14 may be drawn back proximally towards the proximal fitting 30.

Also shown in FIG. 4, the adapter body 12 includes a stop 60 configured to prevent a catheter from extending further proximally into the adapter body 12. An orifice 62 is provided to allow the flow of fluid through the tubular catheter receiver 50 and into a catheter that is inserted in the tubular catheter receiver 50. In this regard, the catheter adapter assembly 10 includes a fluid path 64 defined by the female fitting 52, the orifice 62, the tubular catheter receiver 50, and the catheter insertion guide 24. In some implementations, the inner diameter of the orifice 62 can be substantially smaller than the inner diameter of the tubular catheter receiver 50. The inner diameter of the orifice 62 can be selected based on, for example, the desired flow rate of the fluid passing through the catheter into the patient.

Figure 5:
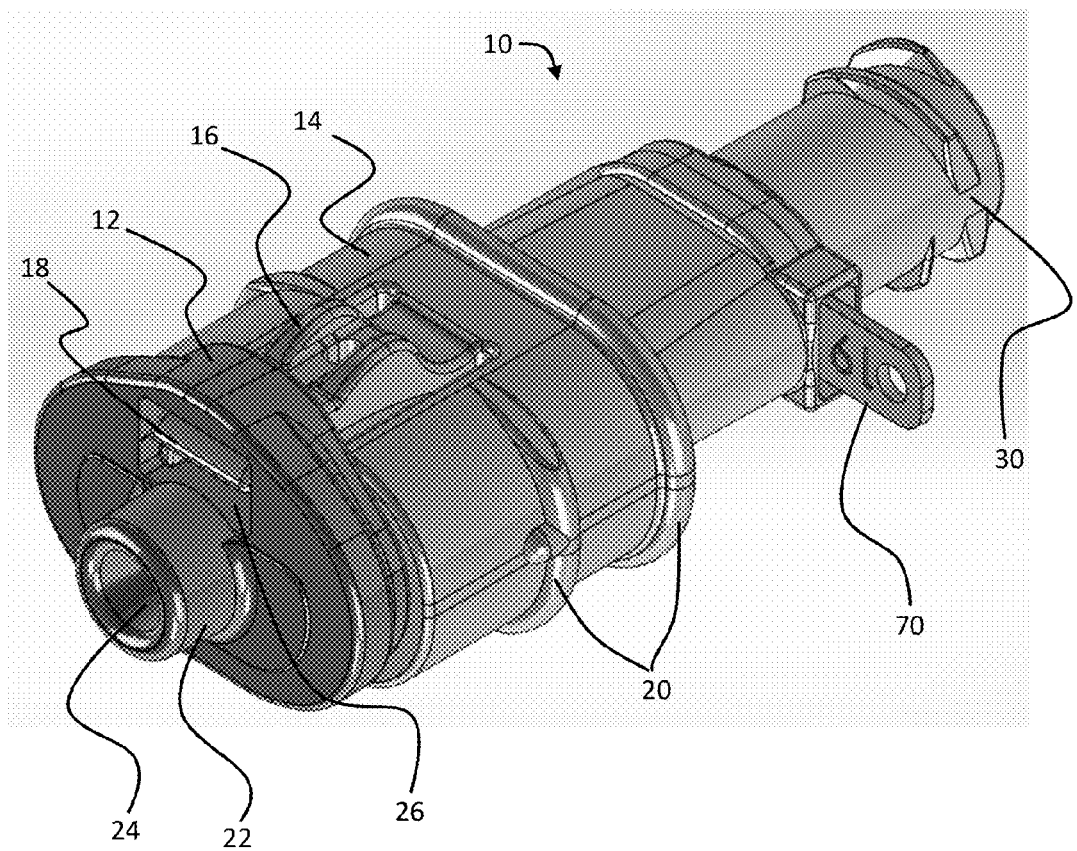
FIG. 5 is a front perspective view of the catheter adapter assembly in the closed position and with a conductive tab according to the implementation of FIG. 1.
Figure 6:
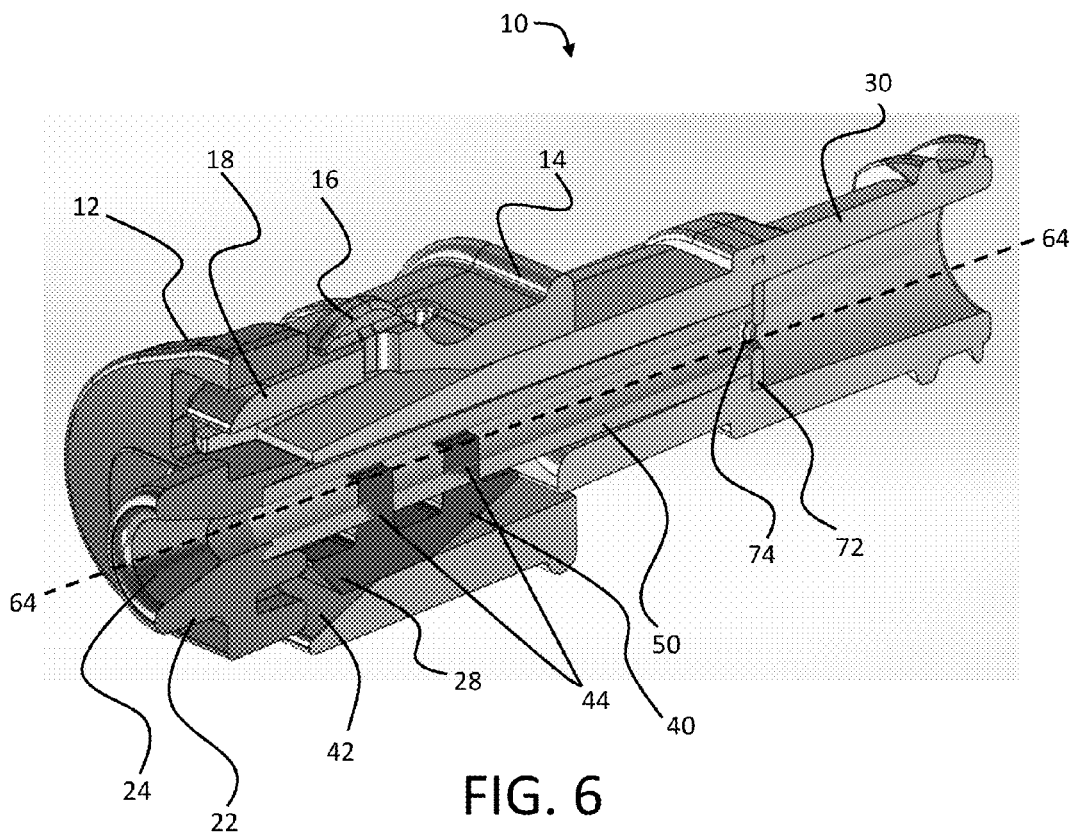
FIG. 6 is a front cutaway perspective view of the catheter adapter assembly in the closed position and with the conductive tab according to the implementation of FIG. 1.

FIG. 5 illustrates a front perspective view of the catheter adapter assembly 10 in the closed position and with an optional conductive tab 70. The conductive tab 70 is configured to allow a practitioner to attach a lead from a stimulator and conduct an electrical stimulus through the adapter body 12 directly into the fluid path 64 shown in FIG. 6. Also shown in FIG. 6, the catheter adapter assembly 10 includes a conductive member 72 having an orifice 74 attached to the conductive tab 70. The conductive member 72 is configured to transmit an electrical stimulus from a source (not shown) connected to the conductive member 72 to a conductive catheter that is inserted though the tubular catheter receiver 50 and in physical contact with the conductive member 72. In some aspects where the catheter adapter assembly 10 does not include the tubular catheter receiver 50, the electrical stimulus can be applied directly to the catheter, while in other aspects, the electrical stimulus can be applied directly to the tubular catheter receiver 50.

Figure 7:
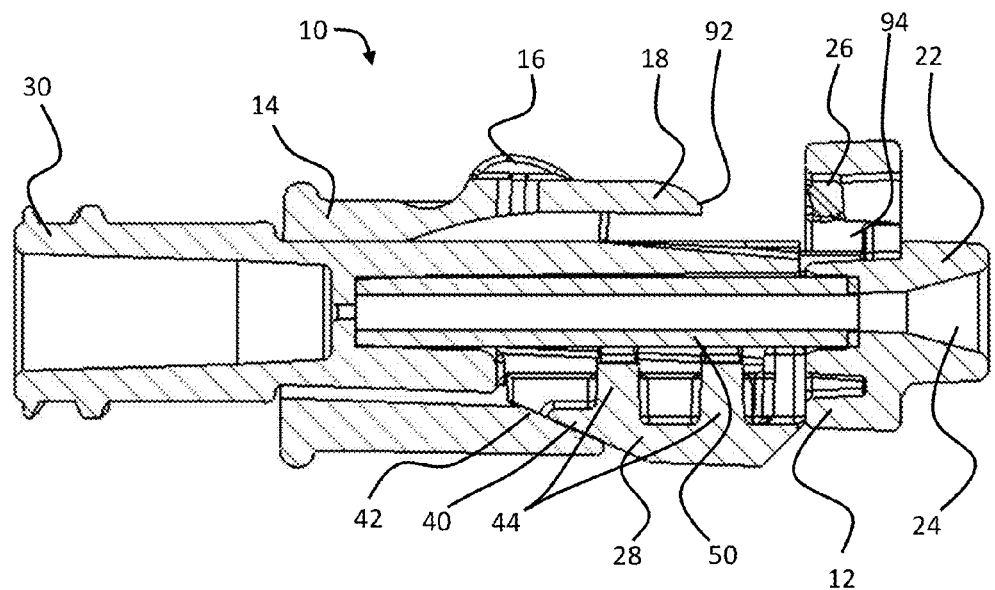
FIG. 7 is a side cutaway view of the catheter adapter assembly in the open position according to the implementation of FIG. 1.
Figure 8:
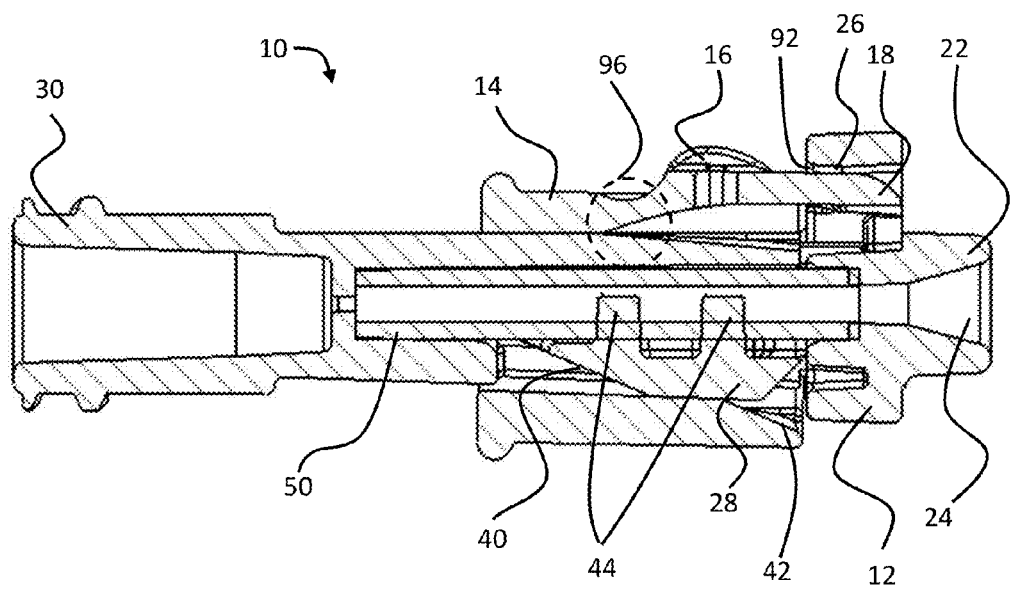
FIG. 8 is a side cutaway view of the catheter adapter assembly in the closed position according to the implementation of FIG. 1.

FIG. 7 illustrates a side cutaway view of the catheter adapter assembly 10 in the open position according to the implementation of FIG. 1. As shown in FIG. 7, when in the open position, the fluid path 64 is configured to receive and guide a catheter. However, as shown in FIG. 8, in response to the slider body 14 distally sliding into the closed position, the grippers 44 urge against the tubular catheter receiver 50, deforming the tubular catheter receiver 50 to urge upon a catheter. In this manner, the catheter may be secured within the fluid path 64 of the catheter adapter assembly 10.

It should be noted that once in the closed position, the slider body 14 is biased to remain in the closed position due to the automatic engagement of the latch 18 with the coupling 26. In this regard, the latch 18 includes a sloped face 90 and the coupling 26 includes a sloped face 92 that urge the latch 18 to deflect downward below the coupling 26 as the slider body 14 slides distally. Once the latch 18 passes the coupling 26, a proximal face of the latch 18 engages a distal face of the coupling 26 because the latch is biased to return upward. As such, the catheter is securely but releasably secured in the fluid path 64.

To release the catheter, the catheter adapter assembly 10 includes a latch recess 94 configured to provide a space for the latch 18 to travel inward. In response to the release 16 being pressed, the flexing portion 96 of the slider body 14 resiliently flexes and the latch 18 is urged into the latch recess 94, at which point the latch 18 is disengaged from the coupling 26. The slider body 14 may then be slid proximally away from the distal end portion 22.

Figure 9:
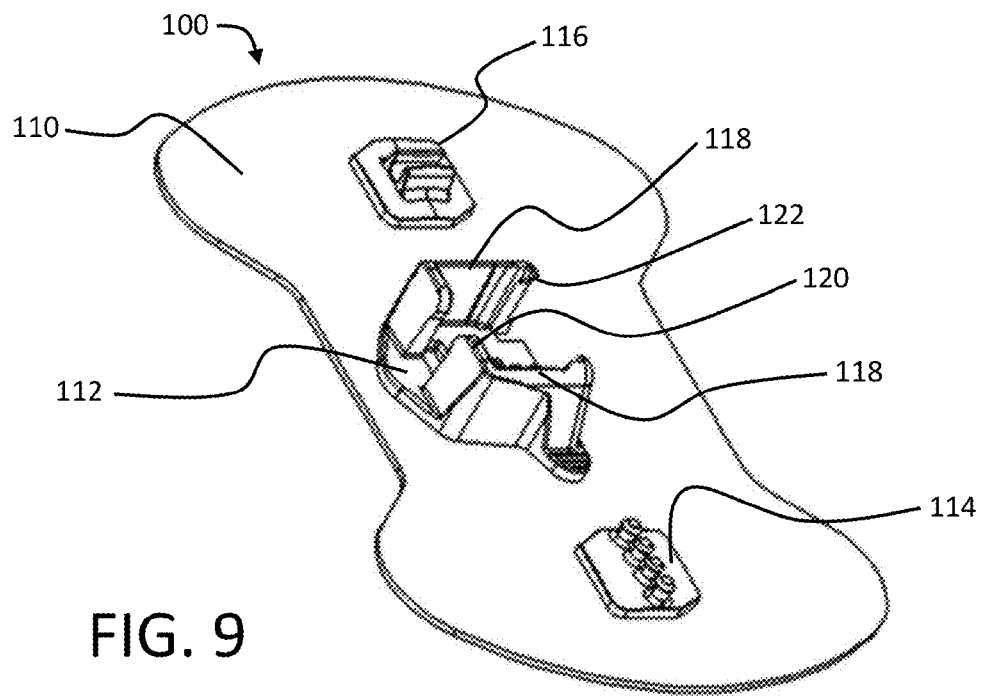
FIG. 9 is a perspective view of a nest suitable for use with the catheter adapter assembly.

FIG. 9 illustrates a perspective view of a nest 100 suitable for use with the catheter adapter assembly 10 according to the implementation of FIG. 1. As shown in FIG. 9, the nest 100 includes a base 110, a receiver 112, the catheter holder 114, and a line holder 116. The base 110 is configured to provide a platform for the various other components of the nest 100 and enables attachment of the nest 100 to a patient. In this regard, the base 110 may include an adhesive of its distal or bottom surface, or may be otherwise attached to a patient or object. The receiver 112 is configured to receive the catheter adapter assembly 10. To retain the catheter adapter assembly, the receiver 112 includes sidewalls 118, forward tabs 120, and rear tabs 122. These elements of the receiver 112 are configured to securely but releasably secure the catheter adapter assembly 10 therein. In some implementations, due to the structure of the receiver 112, it can receive the catheter adapter assembly 10 in the locked position but not in the unlocked position. In this manner, further assurance that the catheter adapter assembly 10 is in the locked position is given.

Figure 10:
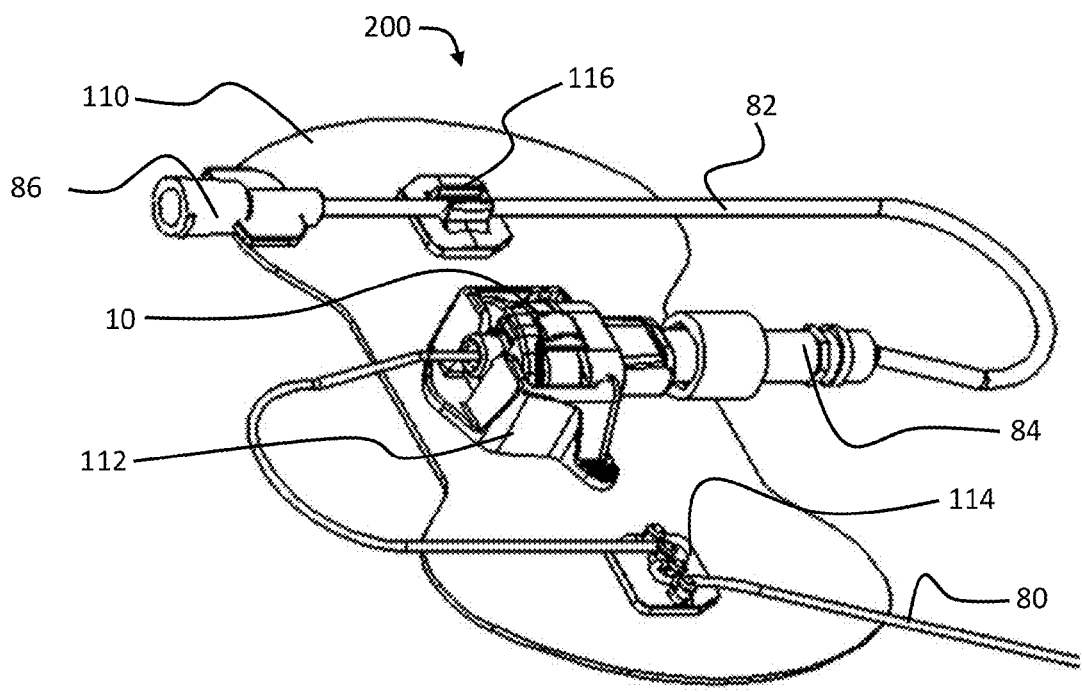
FIG. 10 is a perspective view of a catheter adapter system including the catheter adapter assembly within the nest.

FIG. 10 illustrates a perspective view of a catheter adapter system 200 including the nest 100 and the catheter adapter assembly 10 according to the implementation of FIG. 1. As shown in FIG. 10, the catheter adapter system 200 includes the catheter adapter assembly 10 in the nest 100. In use, the proximal end of the catheter 80 is secured within the catheter adapter assembly 10 and the regions of the catheter between the proximal end and the distal end is secured in the catheter holder 114. In this manner, movement of the catheter 80 may not be transmitted past the catheter holder 114. In addition, a fluid supply line 82 may include a male fitting 84 at its distal end configured to mate with catheter adapter assembly 10. The fluid supply line 82 may include a female fitting 86 at its proximal end. The fluid supply line 82 may be secured to the nest 100 within the line holder 116.

In some implementations, the catheter adapter system 200 may be provided as a kit. In addition to the catheter adapter system 200 including the nest 100 and the catheter adapter assembly 10, the kit may include the fluid supply line 82, the catheter 80, one or more syringes that may be prefilled, adhesive tape or other such device to secure the nest 100 to the patient or to an object, or the like.

The many features and advantages of the catheter adapter assembly and system are apparent from the detailed specification, and thus, it is intended by the appended claims to cover all such features and advantages. Further, since numerous modifications and variations will readily occur to those skilled in the art, it is not desired to limit the catheter adapter assembly and system to the exact construction and operation illustrated and described, and accordingly, all suitable modifications and equivalents may be resorted to.

What is claimed is:

1. A catheter adapter assembly, comprising:
   an adapter body having a proximal end portion and a distal end portion,
   the distal end portion having a center axis and configured to receive a catheter,
   a coupling disposed on the distal end portion,
   a fitting on the proximal end portion configured to connect to a fluid line, and
   a tubular catheter receiver within the adapter body, the tubular catheter receiver comprising an elongated hollow tube made of a deformable material and having a center axis and configured to receive the catheter inside of said elongated hollow tube of said tubular catheter receiver, wherein an inner diameter of the tubular catheter receiver is slightly greater than an outer diameter of the catheter;
   a slider body disposed about the adapter body and configured to axially slide relative to the adapter body, the slider body comprising:
      a release comprising a latch disposed at a distal end of the release and a flexing portion disposed at a proximal end of the release, the latch being configured to engage the coupling of the adapter body to prevent axial movement of the slider body relative to the adapter body; and
   the catheter adapter assembly comprising a compression element configured to compress the elongated hollow tube of said tubular catheter receiver inwards towards the center axis of said elongated hollow tube to hold the catheter in the adapter body in response to axially sliding the slider body distally towards the distal end portion of the adapter body configured to receive the catheter.

2. The catheter adapter assembly of claim 1, wherein the center axis of the elongated hollow tube of the tubular catheter receiver is aligned with the center axis of the distal end portion of the adapter body.

3. The catheter adapter assembly of claim 1, wherein the distal end portion of the adapter body, the tubular catheter receiver, and the fitting of the adapter body are in fluid communication with one another.

4. The catheter adapter assembly of claim 1, further comprising at least one grip on an outer surface of the slider body.

5. The catheter adapter assembly of claim 4, wherein the at least one grip extends radially from an outer surface of the slider body.

6. The catheter adapter assembly of claim 1, wherein the compression element comprises at least one gripper extending radially inward, the at least one gripper having an axial length that is less than an axial length of the compression element.

7. The catheter adapter assembly of claim 1, wherein the release comprises at least one hump between the latch and the flexing portion.

8. The catheter adapter assembly of claim 1, wherein the adapter body further comprises a stop distal of the fitting, wherein the stop is configured to prevent proximal movement of a proximal end of the catheter.

9. The catheter adapter assembly of claim 8, wherein the stop comprises an orifice configured to allow fluid flow through the stop.

10. The catheter adapter assembly of claim 1, wherein the coupling defines a recess formed in the adapter body configured to receive the release of the slider body.

11. The catheter adapter assembly of claim 1, further comprising a conductive tab extending from the adapter body, the conductive tab being configured to conduct an electrical stimulus to the catheter or to fluid flowing within the adapter body in contact with the conductive tab.

12. The catheter adapter assembly of claim 11, wherein the conductive tab is a stop configured to prevent proximal movement of a proximal end of the catheter.

13. The catheter adapter assembly of claim 1, wherein the compression element of the slider body comprises a first sloped face and a flat face directly distal of the first sloped face.

14. The catheter adapter assembly of claim 13, wherein the slider body comprises a second sloped face configured to mate with the first sloped face of the compression element.

15. A catheter adapter system, comprising:
   a catheter adapter assembly comprising:
      an adapter body having a proximal end portion and a distal end portion,
      the distal end portion having a center axis and configured to receive a catheter,
      a coupling disposed on the distal end portion,
      a fitting on the proximal end portion configured to connect to a fluid line, and
      a tubular catheter receiver within the adapter body, the tubular catheter receiver comprising an elongated hollow tube made of a deformable material and having a center axis and configured to receive the catheter inside of said elongated hollow tube of said tubular catheter receiver, wherein an inner diameter of the tubular catheter receiver is slightly greater than an outer diameter of the catheter;
      a slider body disposed about the adapter body and configured to axially slide relative to the adapter body, the slider body comprising:
         a release comprising a latch disposed at a distal end of the release and a flexing portion disposed at a proximal end of the release, the latch being configured to engage the coupling of the adapter body to prevent axial movement of the slider body relative to the adapter body; and
      the catheter adapter assembly comprising a compression element configured to compress the elongated hollow tube of said tubular catheter receiver inwards towards the center axis of said elongated hollow tube to hold the catheter in the adapter body in response to axially sliding the slider body distally towards the distal end portion of the adapter body configured to receive the catheter; and a nest including:
   a base; and
   a receiver configured to receive the catheter adapter assembly on a top side of the base.

16. The catheter adapter system of claim 15, wherein a bottom side of the base comprises an adhesive for securing the base to a patient or an object.

\* \* \* \* \*